United States Patent [19]

Friedman

[11] 4,357,971

[45] Nov. 9, 1982

[54] SYRINGE GAUGING, LOADING AND INJECTION APPARATUS

[75] Inventor: Eliot I. Friedman, Ann Arbor, Mich.

[73] Assignee: Cyberon Corporation, Ann Arbor, Mich.

[21] Appl. No.: 188,739

[22] Filed: Sep. 19, 1980

[51] Int. Cl.³ .............................................. B65B 3/32
[52] U.S. Cl. .................................. 141/27; 141/95; 128/218 C; 222/44; 222/309
[58] Field of Search ............... 128/215, 218 C; 141/2, 141/25, 26, 27, 94, 95, 375; 222/43, 44, 309

[56] References Cited

U.S. PATENT DOCUMENTS

| | | | |
|---|---|---|---|
| 3,965,945 | 6/1976 | Ross | 141/27 |
| 4,252,159 | 2/1981 | Maki | 141/27 |

*Primary Examiner*—John W. Shepperd
*Attorney, Agent, or Firm*—Cullen, Sloman, Cantor, Grauer, Scott & Rutherford

[57] ABSTRACT

A syringe gauging, loading and injection apparatus to enable a person with loss of vision and/or loss of fine motor control to fill a conventional barrel and plunger type syringe with a pre-determined dosage and to thereafter self-inject the dosage from the syringe. The apparatus may be adjusted to the desired dosage and verification of the dosage is accomplished through tactile stimulus and/or audible sound. The apparatus, which releasably supports a syringe, includes a stop member which is positioned by rotation of a wheel to allow the syringe to be filled to the desired dosage. Each complete rotation of the wheel results in a signal to the sense of touch and to the sense of hearing. The stop member may be releasably retained in an operative position, i.e., in engagement with the syringe plunger, to prevent inadvertent emptying of the syringe. The stop member may be releasably retained in an inoperative position, i.e., disengaged from the plunger, when the contents of the syringe are to be discharged such as during self-injection.

7 Claims, 5 Drawing Figures

SYRINGE GAUGING, LOADING AND INJECTION APPARATUS

BACKGROUND OF THE INVENTION

Syringe loading devices, such as the type disclosed in U.S. Pat. No. 3,833,030, are well known. Prior syringe loading devices required a person with normal vision to initially set the device at a prescribed dosage. Additionally, it was necessary to remove the syringe from these prior art devices so that the contents of the syringe could be injected.

Thus, prior to the present invention, syringe loading devices required a person with normal vision to set the device at the proper dosage. Hence persons with impaired vision, who were required to change the dosage, required the assistance of a person with normal vision and these devices were of only limited utility to persons without normal vision.

Furthermore, according to the prior art, after the syringe was loaded, there was no recognition of the problem of partial discharge of the syringe contents because of inadvertent syringe plunger movement prior to injection of the dosage from the syringe. This problem was occasioned, at least in part, by the necessity of removing the syringe from the prior art loading devices prior to the injection of the dosage from the syringe.

In addition, the prior art loading devices typically were adjusted by persons having normal fine motor control. It is well known, however, that loss of fine motor control is often associated not only with aging but also with partial spasticity and with diabetes.

The present invention overcomes the problems of the prior art syringe loading devices by providing a new and improved syringe gauging, loading and injection apparatus.

SUMMARY OF THE INVENTION

The present invention provides a syringe gauging, loading and injection apparatus that may be adjustably set to an exact dosage by a person with impaired vision and/or loss of fine motor control. Adjustment of the syringe dosage, referred to as gauging, is verified through tactile stimulus and through audible stimulus.

The present invention further provides a means for releasably retaining the syringe plunger in position after the syringe has been filled to prevent accidental discharge of the syringe contents prior to injection of the syringe contents.

BRIEF DESCRIPTION OF THE DRAWINGS

The foregoing objects and advantages of the present invention, together with other advantages which may be attained by its use, will become more apparent upon reading the following detailed description of the invention taken in conjunction with the drawings.

In the drawings, wherein like reference numerals identify corresponding parts.

DETAILED DESCRIPTION OF THE INVENTION

Figure 1:
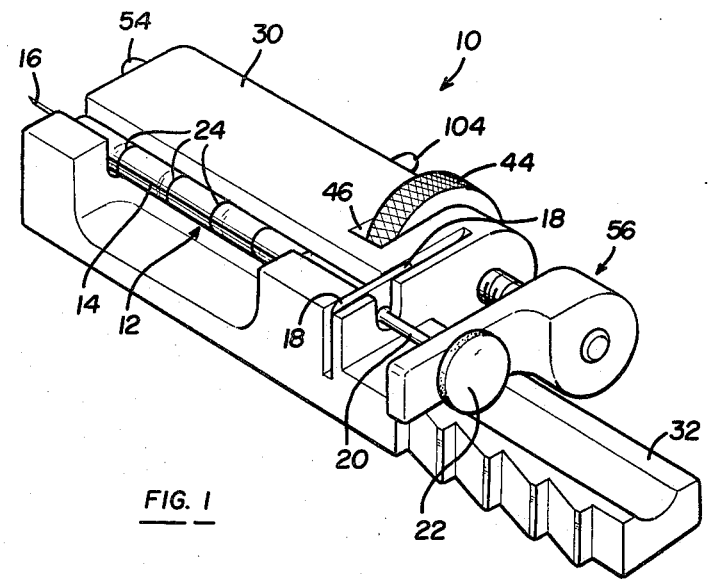
FIG. 1 is a perspective view of a syringe gauging, loading and injection apparatus of the present invention and includes a syringe positioned within the apparatus and illustrates a stop member in engagement with the syringe.
Figure 2:
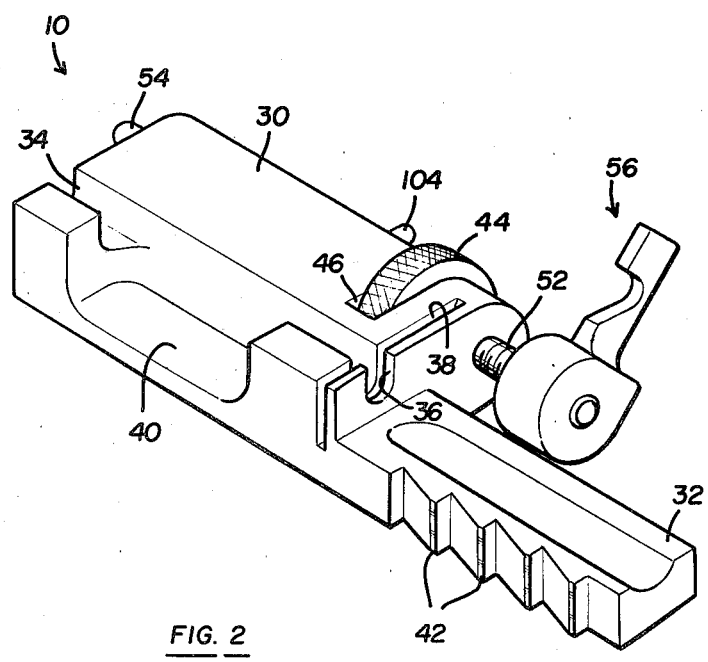
FIG. 2 is a perspective view of the syringe gauging, loading and injection apparatus of the present invention with the stop member in the inoperative position and with the syringe removed.
Figure 3:
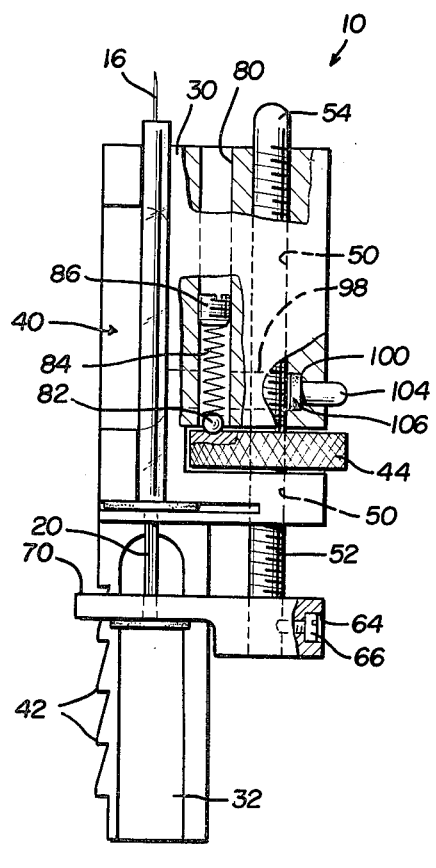
FIG. 3 is a plan view, partially broken away, of the syringe gauging, loading and injection apparatus of the present invention.

Referring to the drawings, a syringe gauging, loading and injection apparatus 10 of the present invention is adapted to releasably support a conventional syringe 12 of the barrel and plunger type. Such a syringe 12 is typically of the disposable type and is utilized for injection of insulin. The syringe includes a barrel 14 having a needle 16 extending outwardly from one end of the barrel and the opposite end of the syringe barrel includes outwardly extending flanges or finger grips 18. The syringe includes a plunger 20 which moves slidably within the barrel 14 and the plunger 20 includes an enlarged plunger head 22 external to the plunger barrel. As his conventional, the syringe barrel 14 includes a plurality of indicia 24 for ascertaining the dosage retained within the syringe. Typically, for an insulin syringe, the indicia are in the form of units of insulin. Alternatively, the indicia may refer to the volume of the dosage within the syringe in cubic centimeters.

In order to understand the various advantages of the present invention, the preferred mode of filling and discharging a syringe should first be understood. The preferred technique for filling a syringe with the proper dosage is to insert the syringe needle through the conventional diaphragm of a vial, and generally invert the vial so that the syringe is in an inclined or vertical position with the needle at the uppermost end of the syringe. The plunger head 22 is gripped, typically with the fingers, and withdrawn beyond the desired dosage level to over-fill the syringe. The syringe needle is withdrawn from the vial and the syringe plunger is depressed toward the needle by pressing, typically with the thumb on the plunger head 22, to expel any air in the syringe and to expel any excess dosage from the syringe. Thus the syringe contains the desired dosage with no air bubbles. Thereafter, of course, the syringe needle is inserted into the skin and the plunger depressed toward the needle to completely inject the dosage from the syringe.

Thus it may be appreciated that the proper technique for utilizing a syringe includes initially over-filling the syringe, thereafter expelling any air and any excess dosage from the syringe, and finally injecting the dosage.

With that preferred technique in mind, the following explanation of the apparatus of the present invention may be more easily understood. The apparatus of the present invention, which may be made of light weight metal or plastic, includes an elongated generally rectangular body portion 30 having opposed first and second ends and opposed first and second longitudinal sides. The body includes an extension 32 which extends outwardly from the second body end, longitudinally of the body 30, and at the first side of the body. The upper face of the body, adjacent the first side thereof, is provided with means for releasably holding the syringe. Specifically, a first semi-circular recess 34 is provided at the first end of the body 30 and a second semi-circular recess 36 is provided at the second end of the body. The recesses 34 and 36 are longitudinally spaced apart to receive opposite ends of the syringe barrel 14 and, therefore, are longitudinally aligned with each other. A slot 38 is provided in the face of the body 30 transversely of and intersecting the second recess 36 to receive the finger grip or flange 18 of the syringe. The syringe is precisely positioned within the body 30 by the two recesses 34, 36, each of which frictionally retains opposite ends of the syringe barrel 14, and by the slot 38 which frictionally retains the finger grip 18 of the syringe barrel. In addition, an elongated notch 40 is provided along the first side of the body 30 intermediate the recesses 34 and 36 to provide access to the underside of the syringe and thereby facilitate removal of the syringe from the body 30.

The body extension 32 extends longitudinally of the body 30 and is aligned with the longitudinal axis of the recesses 34 and 36. The body extension 32 is thinner than the body 30 thus providing a clearance for the enlarged plunger head 22 as the plunger and plunger head are withdrawn from the syringe. The body extension 32 has a plurality of uniformly spaced apart teeth 42 formed therein. The longitudinal spacing between these teeth 42 corresponds to the spacing between the indicia 24 on the syringe barrel. Thus if the syringe barrel is marked in cubic centimeters with major markings every 10 cubic centimeters, as is conventional, then each of the teeth 42 are spaced apart a distance such that movement of the plunger head between any two adjacent teeth corresponds to a 10 cubic centimeter change in the volume within the syringe. By way of further example, if the syringe barrel capacity is three cubic centimeters, the spacing between adjacent teeth could correspond to a one-half cubic centimeter change in volume within the syringe. This is explained in greater detail hereafter.

The apparatus includes means for gauging or adjusting the dosage of the syringe including a knurled adjustment wheel 44 positioned in a slot 46 in the body. The wheel 44 has an axial threaded centering hole 48 therethrough and the wheel has a diameter greater than the thickness of the body 30.

A first bore 50 extends through the body 30 from the first end to the second end substantially adjacent the second longitudinal side of the body. An elongated shank 52 threaded substantially along its length, except at its first end 54, is inserted through the bore 50. The diameter and threading of the shank 52 corresponds to the diameter and threading of the hole 48 within the wheel 44 such that the wheel may be threaded onto and thereby mounted on the shank 52. The first end of the shank 54, which is not threaded, is positioned toward the first end of the body 30.

With the shank 52 positioned in the first bore 50 and the wheel 44 threaded on the shank and mounted within the slot 46, the shank 52 is of sufficient length to extend beyond the second end of the body 30. At the second or threaded end of the shank 52 a stop member 56 is provided. The stop member 56 has an internally threaded bore 58 to receive the threaded shank 52.

The stop member 56 has a generally circular first portion 60, which contains the threaded bore 58, and a generally flat extension or second portion 62. The stop member 56 also includes a countersunk hole 64 which hole is internally threaded to receive a threaded screw 66. The countersunk hole is positioned in the first portion of the stop member 60, transversely of the stop member bore 58 so that upon tightening the screw 66, the end of the screw engages the shank 52 within the bore 58 to positively secure the stop member 56 onto the shank 52.

Thus it may be appreciated that upon rotation of the wheel 44 in a first direction, the shank 52 moves longitudinally of the body 30 in a first direction and the stop member 56 also moves longitudinally of the body 30 because the stop member is secured to the shank 52. In addition, since the bore 50 is not threaded but since the hole 48 in the wheel 44 is threaded, the wheel 44 may be held in a fixed position and the stop member 56 rotated. In addition, upon rotation of the wheel 44 in the first direction, the stop member 56 will be moved away from the body and upon rotation of the wheel 44 in the opposite or second direction, the stop member 56 will be moved toward the body until it engages the second edge of the body 30.

When the wheel 44 is rotated in the first direction, the stop member 56 will be moved away from the body until the unthreaded first end of the shank 54 reaches the threaded hole 48 of the wheel 44 at which point the absence of threads on the shank precludes further rotation of the wheel. This prevents inadvertent disassembly of the apparatus.

As indicated previously, the stop member 56 includes a generally circular thin disc like first portion 60 and a second portion 62 which is a flat extension of the first portion. The stop member, including the first and second portions, includes a front face 70 which is defined as the face of the stop member positioned closer to the body 30, and an opposed rear face 72. A notch 74 is provided in the second portion 62 of the stop member 56 generally parallel to the bore 58 in the stop member 56 and spaced apart therefrom a sufficient distance so that when syringe is positioned in the apparatus of the present invention and the stop member rotated counterclockwise, the notch fits over the plunger 20 of the syringe. This is referred to as the operative or engaged position of the stop member. When the stop member is rotated clockwise about the shank 52, the notch is no longer engaged with the plunger 20 and this is referred to as the disengaged or inoperative position of the stop member. With the stop member in the engaged or operative position, i.e., with the notch 74 positioned over the plunger 20, inward movement of the plunger head 22 is limited by the abutting contact of the plunger head with the rear face 72 of the stop member.

Since rotation of the wheel 44 causes the stop member 56 to move longitudinally of the body, and since the rear face 72 of the stop member limits the travel of the syringe plunger when the stop member is in the operative position, it must be appreciated that rotation of the wheel 44 permits gauging or setting the dosage of the syringe. More specifically, consider the situation where the first tooth 42 on the body extension 32 corresponds to 10 units in the syringe. If it is desired to fill the syringe with 10 units, then the wheel 44 is rotated until the rear face 72 of the stop member is aligned with the first tooth 42. The syringe is inserted in the vial and the plunger withdrawn until the plunger head 22 extends beyond the first tooth 42. The stop member is rotated into the operative position and the plunger depressed until the plunger head 22 engages the rear face 72 of the stop member. At this physical positioning the syringe will contain exactly 10 units. Thereafter, upon rotating the stop member out of the operative position, the plunger may be depressed to eject the dosage from the syringe.

Thus through tactile stimulus, i.e., physically feeling the alignment between the rear face 72 of the stop member and the teeth 42, the dosage in the syringe may be gauged or adjusted.

It may be understood, therefore, that a relationship exists relative to the capacity of the syringe, the spacing of the teeth 42, and the pitch of the threads of shank 52. For example, a 3 cubic centimeter syringe could be used with a large pitch threaded shank 52 so that each revolution of the wheel 44 corresponds to a change in dosage of one-half cubic centimeter and the teeth 42 could be spaced apart corresponding to a one cubic centimeter change in volume. Hence two revolutions of the wheel 44 corresponds to the distance between adjacent teeth. Hence the spacing of the teeth as well as the pitch of the shank may be varied to accommodate the particular needs of the user.

According to the principles of the present invention, both audible and tactile stimuli are provided for adjusting or gauging the dosage within the syringe. Specifically, the apparatus includes a second bore 80 within the body 30 parallel to the bore 50 and spaced apart therefrom with the bore 80 being positioned intermediate the bore 50 and the aligned recesses 34, 36. The bore 80 extends from the first end of the body to the slot 46 and the lower half of the bore 80, i.e., the portion of the bore closer to the slot 46 is internally threaded. A small metal ball 82 is positioned in the bore 80 and urged toward the wheel 44 within the slot 46 by spring means 84. A set screw 86 threaded within the bore 80 retains the spring in slight compression.

Figure 4:
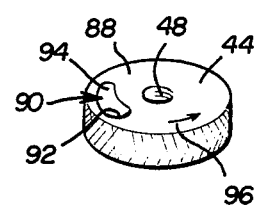
FIG. 4 is a perspective view of the adjustment wheel which is part of the present apparatus.
Figure 5:
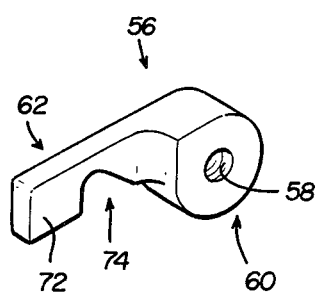
FIG. 5 is a perspective illustration of the stop member which is part of the present apparatus.

Means are provided to coact with the ball 82 to provide both audible and tactile stimuli upon rotation of the wheel 44. Specifically, the wheel 44 has a front surface 88 having a notch 90 therein. The spacing between the notch 90 and the hole 48 in the wheel 44 corresponds to the distance between the bore 50 and the bore 80 such that the ball 82 is resiliently urged toward the notch 90. The notch 90 is tapered gradually to be of greater depth at the first end 92 thereof relative to the depth at the second end 94 of the notch. Thus the bottom surface of the notch is formed as a ramp. When the wheel 44 is positioned within the slot 46, the front surface 88 of the wheel is positioned in the slot facing the bore 80 so that the ball 82 presses against the front surface 88 of the wheel and, upon rotation of the wheel, the ball 82 moves into the notch as the notch moves past the bore 80. Each single rotation of the wheel 44 corresponds to a preselected change in volume within the syringe 12. With the spring means 84 urging the ball against the face of the wheel, as the wheel is rotated counterclockwise, as illustrated generally by the arrow 66 in FIG. 4, the ball 82 engages the deeper end 92 of the notch 90 and then rides up the ramp or taper of the notch and out of engagement with the notch 90. This engagement of the ball 82 with the notch 90 provides an audible noise as well as a tactile stimulus with the audible noise and tactile stimulus each being of a first intensity. Movement of the wheel 44 in this counterclockwise direction serves to move the stop member 56 away from the body 30 to thus increase the dosage within the syringe.

Upon rotation of the wheel 44 in a clockwise direction, i.e., opposite to the direction of arrow 96, upon each rotation of the wheel the ball engages the notch 90 starting at the more shallow end 94 of the taper, and then riding down the tapered notch to the deeper second end 94 of the notch. This provides an audible stimulus and a tactile stimulus each of which is at a second level of intensity lesser than the first level of intensity. Since the clockwise motion of the wheel 44 moves the stop member 56 toward the body 30 thus decreasing the dosage, it may be appreciated that a louder sound, as well as a greater intensity tactile stimulus occurs upon each rotation of the wheel which increases the dosage.

By this technique, persons with impaired vision, through the use of both audible and tactile stimuli, may adjust the dosage of the syringe with each rotation of the wheel corresponding to a desired change in volume within the syringe and with each rotation of the wheel providing both audible and a tactile stimuli. The intensity of these stimuli indicate the direction of movement of the wheel and stop member and thus indicates whether the dosage has been increased or decreased.

As heretofore explained, rotation of the wheel 44 causes rotation of the stop member 56. When the wheel is rotated in the clockwise direction, the stop member is rotated in the clockwise direction until it engages the body extension 32. Thereafter, rotation of the wheel can continue but the stop member will not rotate because of the engagement of the stop member second portion 62 with the body extension 32. Similarly, rotation of the wheel 44 in the counter-clockwise direction will move the stop member 56 out of engagement with syringe plunger into the inoperative position and the stop member rotates with the wheel until the stop member contacts the underside of the body extension 32. Thereafter the stop member does not rotate any further notwithstanding the continued rotation of the wheel 44.

It may be appreciated, therefore, that slight inadvertent movement of the wheel and/or the stop member may occur during the steps of filling the syringe and expelling excess air and dosage from the syringe. Means are provided to maintain the stop member in either the operative or inoperative position and to prevent inadvertent movement of the stop member to thereby avoid accidental emptying of the contents of the syringe. Specifically, the body 30 is provided with a third bore 98 extending transversely of the bores 50 and 80 and positioned in the body adjacent the slot 46 and closer to the first end of the body 30 than the slot 46. This bore 98 extends across the body 30 and includes an internal shoulder 100 adjacent the second longitudinal side of the body intermediate the bore 50 and the second side of the body. The bore 98 continues to the second side of the body past the internal shoulder 100 with the portion of the bore extending beyond the internal shoulder 100 being of narrower diameter. A plastic detent 104 is mounted within the bore 98. The plastic detent has an enlarged head 106 which fits within the bore 98 and is retained by the internal shoulder 100 within the bore. The detent 104 extends outwardly of the bore and beyond the second longitudinal side of the body 30. Upon manually pressing the detent 104 the enlarged detent head 106 engages the shank 52 within the bore 50 to prevent rotation of the shank. Restricting or preventing rotation of the shank prevents inadvertent changing of the dosage and thus prevents inadvertent emptying of the contents of the syringe as follows. Once the wheel 44 is rotated to the desired dosage, the detent 104 is depressed so that the detent head 106 engages the shank 52. The stop member is manually moved into the inoperative or disengaged position. The syringe needle 16 is inserted into a vial and the plunger head 22 withdrawn to overfill the syringe. The detent is released and the stop member 56 rotated into the operative or engaged position. The detent 104 is again depressed to engage the shank 52 and the plunger head 22 moved inwardly to engage the rear face 72 of the stop member thus expelling any air and excess dosage from the syringe. The needle 16 is then inserted into the skin, the detent 104 released and the stop member 56 rotated into the inoperative position. Thereafter the plunger head 22 is pushed inwardly toward the barrel to empty the contents of the syringe by self-injection. Thus it may be appreciated that the use of the detent 104 prevents inadvertent movement of the wheel and thus prevents inadvertent changing of the dosage or inadvertent discharge of the syringe contents.

Once the desired dosage has been established by rotation of the wheel 44, it is anticipated that the user of the apparatus of the present invention will use the apparatus repeatedly without any change in dosage. To prevent inadvertent rotation of wheel 44, screw 86 may be advanced toward wheel 44 thus tightly compressing spring 84 and creating a tight fit of the ball 82 within the notch 90. This tight friction fit precludes inadvertent movement of wheel 44. Alternatively, the ball and spring may be replaced by a short cylindrical stud which is held in frictional engagement with wheel 44 by tightening set screw 86. Thus the present invention also contemplates locking the apparatus at a desired dosage.

The foregoing is a complete description of a preferred embodiment of the present invention. Various changes and modifications may be made by those skilled in the art without departing from the spirit and scope of the present invention. The invention, therefore, should be limited only by the scope of the following claims.

What is claimed is:

1. In a syringe gauging, loading and injection apparatus for a conventional syringe of the barrel and plunger type, said apparatus including a body for releasably supporting a syringe and an adjustable stop member for limiting the travel of the syringe plunger, the improvement comprising:
    said body including aligning means for supporting said syringe with said syringe barrel in a fixed position relative to said body and with said syringe needle extending clear of said body;
    means for adjusting the position of said stop member relative to said fixed barrel position so that said stop member may be used to vary the dosage of the syringe;
    said stop member position adjusting means including means for producing first audible and first tactile stimuli upon increasing the distance between said fixed barrel position and said stop member;
    said stimuli producing means also producing second audible and second tactile stimuli upon decreasing the distance between said fixed barrel position and said stop member;
    said first audible and tactile stimuli being of a different intensity than said second audible and tactile stimuli;
    said adjustable stop member having an operative position and an inoperative position;
    means for movably mounting said stop member so that said stop member may be moved between said operative and inoperative positions;
    said stop member inoperative position being free of engagement will said plunger for allowing alternate filling of said syringe and thereafter emptying of said syringe by movement of said plunger;
    said stop member operative position for limiting the extent of travel of said syringe plunger toward said syringe barrel fixed position for allowing partial emptying of said syringe so that the contents of the syringe may be reduced to the desired dosage and also to expel any air in said syringe prior to injecting said dosage; and
    said apparatus body for also supporting said syringe while said dosage is being injected.

2. The invention as defined in claim 1 wherein said first stimuli are of greater intensity than said second stimuli.

3. The invention as defined in claim 1 wherein said stop member position adjusting means is operably connected to said stop member, for adjusting the distance between said stop member and said body.

4. The invention as defined in claim 1 wherein said stimuli producing means includes a rotatable wheel and a movable member resiliently urged against said wheel;
    said wheel including a notch for engagement with said movable member upon each complete rotation of said wheel, the engagement of said movable member with said wheel creating said audible and tactile stimuli;
    said engagement providing said audible and tactile stimuli of different intensity based upon the direction of rotation of said wheel.

5. The invention as defined in claim 1 wherein said stop member position adjusting means further includes detent means for frictionally retaining said stop member position adjusting means in a preselected position.

6. The invention as defined in claim 1 wherein said stop member position adjusting means further includes an extension on said body member, said extension having a plurality of spaced apart tactile indicia; the spacing between the adjacent tactile indicia corresponding to selected dosages; said spaced apart tactile indicia forming an indicator.

7. The invention as defined in claim 1 wherein said stop member position adjusting means further includes resilient means for retaining said stop member position adjusting means in a desired position.

* * * * *